United States Patent [19]

Leary

[11] 4,347,732

[45] Sep. 7, 1982

[54] GAS MONITORING APPARATUS

[76] Inventor: David J. Leary, 2832 Eagle Dr., Ft. Collins, Colo. 80526

[21] Appl. No.: 179,218

[22] Filed: Aug. 18, 1980

[51] Int. Cl.³ .............................................. G01N 27/12
[52] U.S. Cl. ......................................... 73/23; 338/34
[58] Field of Search ................... 73/23, 27 R; 338/34, 338/35; 422/98; 55/389

[56] References Cited

U.S. PATENT DOCUMENTS

| | | | |
|---|---|---|---|
| 3,428,892 | 2/1969 | Meinhard | 338/34 |
| 3,831,432 | 8/1974 | Cox | 73/23 |
| 3,865,550 | 2/1975 | Bott et al. | 73/23 |
| 3,901,067 | 8/1975 | Boardman Jr. et al. | 73/23 |
| 3,924,219 | 12/1975 | Braun | 338/34 |
| 4,239,516 | 12/1980 | Klein | 55/389 |

OTHER PUBLICATIONS

J. N. Zemel, "Ion-Sensitive Field Effect Transistors and Related Devices", *Analytical Chemistry*, vol. 47, No. 2, pp. 255A-268, Feb. 1975.

J. S. Maudes et al., "Growth and Structure in Sprayed $SnO_2$ Films", *Thin Solid Films*, pp. 183-189, 1980.

J. Aranovich et al., "Optical and Electrical Properties of ZnO Films Prepared by Spray Pyrolysis for Solar Cell Applications", *J. Vac. Sci. Tech.*, 16(4), pp. 994-1003, Jul./Aug. 1979.

N. Ichinose et al., "Ceramic Oxide Semiconductor Elements for Detecting Gaseous Components", 11(3), pp. 203-211, 1976.

*Primary Examiner*—Stephen A. Kreitman
*Attorney, Agent, or Firm*—Hugh H. Drake

[57] ABSTRACT

A pair of electrodes are spaced apart on an electrically-insulating support surface. Disposed on the surface in a position bridging the electrodes is a sensor that exhibits a change in conductivity in response to exposure of the material to a wide variety of certain flammable and toxic gases. Overlying the sensor is a molecular sieve passivation layer composed of a porous solid material that has a pore size no larger than the molecular size of the gas to be sensed. The molecular sieve passivation layer can be incorporated onto various solid state and catalytic-type gas sensors, including metal oxide based solid-state sensors such as, for example, those of a zinc oxide base. With or without the sieve, the most salient form of zinc oxide based sensor is zinc oxide doped with gallium oxide. It is expedient to use such improved sensors as a discrete device or in a hybrid array for environmental ambient qualification as incorporated into a portable instrument.

8 Claims, 3 Drawing Figures

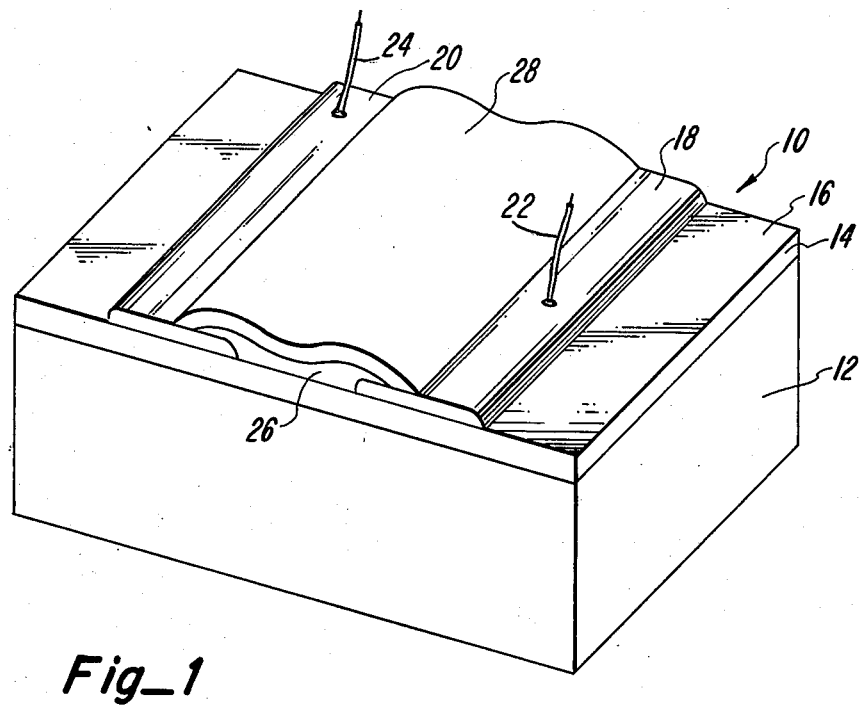
Fig_1
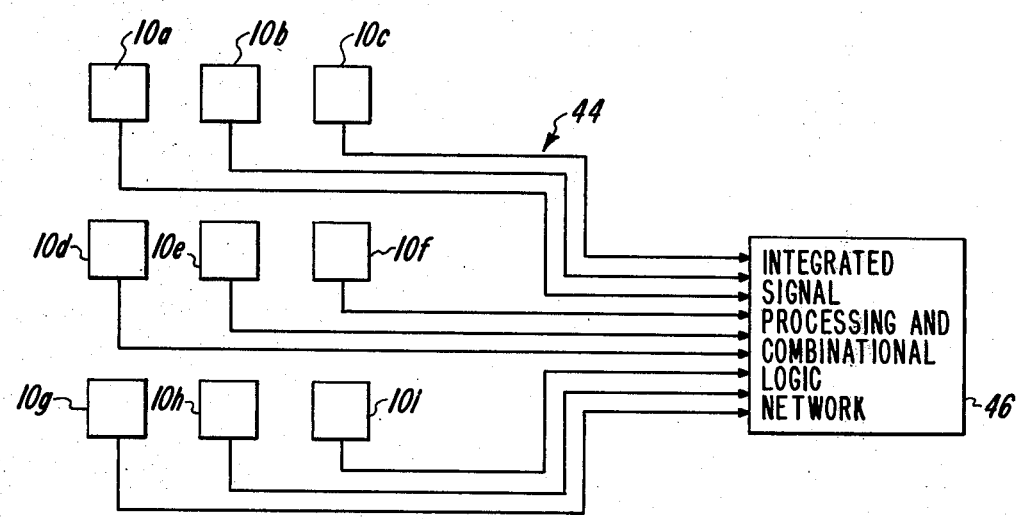
Fig_3

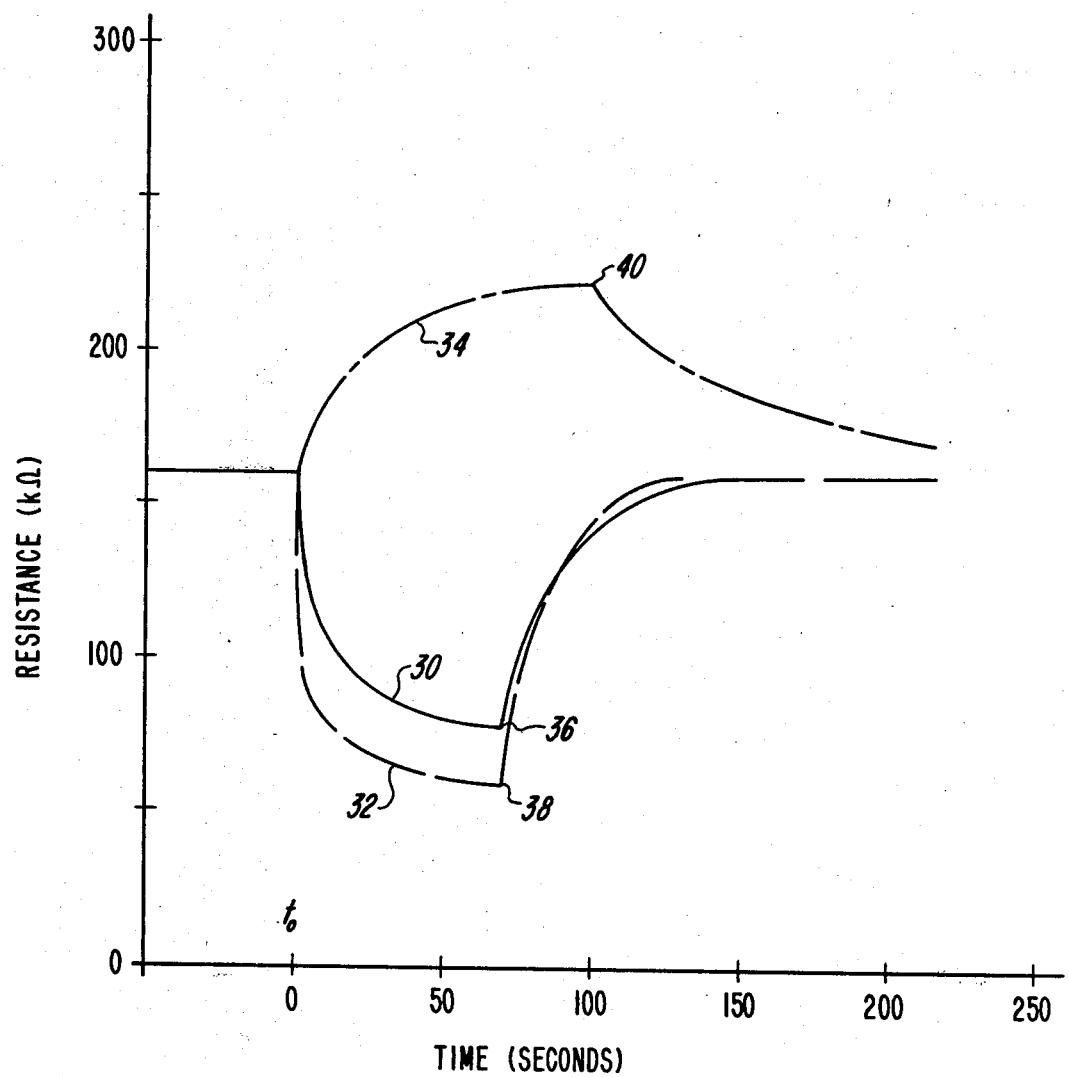
Fig_2

GAS MONITORING APPARATUS

The present invention pertains to gas monitoring apparatus. More particularly, it relates to solid state semiconductor devices capable of detecting and discriminating low concentrations of flammable and toxic gases.

The lack of portable individual air pollution monitors for, the increasing awareness of health hazards of, and the lack of knowledge of the effects on health of individual exposures to air contaminants has sparked national concern for the development of environmental air pollution monitors for detection and discrimination of flammable and toxic gases in individual portable instrumentation. One of the major developmental problems faced by manufacturers for cost effective instrumentation is a compatible gas sensing technology. That is, there is a need for a gas sensing technology which lends itself to the development of highly sensitive gas sensors that can detect and discriminate low concentrations of flammable and toxic gases consistent with threshold limit and time-weighted-average values prescribed by health effects regulations and in a reliable, low cost manner for portable systems.

One technology that has shown significant promise in the laboratory involves electrical conductivity changes in semiconducting devices caused by electrochemical interactions of solid surfaces with adsorbed gas species. Exemplary of that technology are U.S. Pat. Nos. 3,831,432-Cox and 3,901,067-Broadman, Jr. et al as well as an article entitled "Ion Sensitive Field Effect Transistors and Related Devices" by J. N. Zemel appearing in *Analytical Chemistry*, Volume 47, Number 2, February 1975, pp. 255A-268A.

Many commercially available gas sensing devices utilize older technologies that are deficient in not readily lending themselves to portable instrumentation, particularly because of incompatibility with integration on silicon. Many solid state sensors which have thus far been proposed suffer from poor selectivity and non-linear response characteristics. Instrumentation which has been proposed for utilizing such sensors requires complex and costly signal processing and analytical capability. Approaches which have attempted to incorporate selectivity within a solid state sensor by utilizing chemically selective films, or an array of identical devices operated at different temperatures, have suffered from short term selectivity degradation and stability deterioration.

The non-linear response characteristics of a gas sensitive semiconducting device to a particular gas constituent are generally well known and can be readily interpreted by standard low cost signal processing in a portable instrument. However, in the more common situation where a multiplicity of gas constituents are present, selectivity and stability in this technology must be improved significantly. Indeed, solid state sensors which respond to only single gas species and exhibit long term stability and reproducibility are desirable. However, absolute selectivity is not required.

It will be shown herein that cost effective portable instrumentation can be realized utilizing solid state device technology with sensors incorporating molecular sieve passivation layers which screen out gas constituents from the sensor based on molecular size. Sensor selectivity is then enhanced by this separation of gas constituents. Sensor lifetime and stability are improved in many cases by screening out gases which effect deterioration of response characteristics. Sensor sensitivity is improved in many cases by minimizing or eliminating sensor cross-sensitivity to secondary gas constituents. Sensor response time is not degraded.

It is a general object of the present invention to provide new and improved gas monitoring apparatus that overcomes various deficiencies hereinabove discussed.

In general, it is well known that semiconductor surfaces are influenced by the nature of adsorbed impurities. Indeed, this is basic to the solid state gas sensor technology mentioned above. However, in many other areas of solid state technology, such adsorption is undesired. Accordingly, the exterior surfaces of integrated devices are passivated in order to preclude such effects. As embodied in this present invention, and as related to solid state gas sensors, passivation utilizes molecular sieve materials which preferentially allow certain gas constituents to pass to the sensor and preclude adsorption of other gas constituents. The basis for this separation is molecular size.

Accordingly, another object of the present invention is to provide new and improved gas monitoring apparatus for discriminating among low concentrations of different gases.

A further object of the present invention is to provide a new and improved sensor for gas monitoring.

Yet another object of the present invention is to provide new and improved gas monitoring apparatus that benefits from planar processing techniques heretofore developed in the semiconductor art.

Other specific objects of the present invention with respect to gas monitoring apparatus include: (1) capability of processing consistent with silicon planar integrated circuit techniques, (2) adaptability of devices for use either as a discrete or in a hybrid array, (3) capability of response to gas constituents in the ambient while yet exhibiting long term stability and reproducibility, (4) operation in a manner representing the electrical analog of a low-pass filter so as to provide (or allow) simple decoding in a system which responds to an array of such apparatus, (5) achievement of discrimination of gas constituents utilizing existing processing techniques available in integrated circuit technology for the disposition of passivation layers, (6) adaptability for incorporation into a fully integrated portable environmental monitoring system which yet requires only the use of standard integrated circuits and processing and (7) improved processing techniques for enabling optimization of sensor characteristics.

In accordance with one principal feature of the present invention, gas monitoring apparatus comprises a support which includes an electrically insulating surface spaced apart on which are a pair of electrodes. Disposed on the surface, in a position bridging the electrodes, is a sensor composed of a material which exhibits a change in conductivity in response to exposure of that material to a gas to be sensed. A molecular sieve overlies the sensor on the side thereof opposite the surface with the sieve being composed of a porous solid material that has a pore size no larger than the molecular size of the gas to be sensed.

Another feature of the invention involves such a gas sensor itself. In particular, the sensor consists essentially of zinc oxide doped with gallium oxide as an impurity.

The features of the present invention which are believed to be patentable are set forth with particularity in the appended claims. The organization and manner of operation of the invention, together with further objects and advanatages thereof, may best be understood by reference to the following description taken in connection with the accompanying drawings, in the several figures of which like reference numerals identify like elements, and in which:

FIG. 1 is an isometric view of one embodiment of a gas monitoring device;

FIG. 2 is a plot of exemplary operational characteristics; and

FIG. 3 is a block diagram of a system which utilizes devices such as those shown in FIG. 1.

In accordance with a preferred embodiment, a gas monitoring device 10 includes a substrate 12 on which has been formed an insulating layer 14. Substrate 12 is of silicon, and its insulating layer 14 presents an upper surface 16. Layer 14 is the electrical insulator.

Substrate 12 and its layer 14 together constitute a support which carries a pair of conductive electrodes 18 and 20 individually to each of which are connected respective leads 22 and 24 that extend to associated apparatus as will be discussed more fully in connection with FIG. 3.

A sensor 26 is disposed on surface 16 in a position to bridge electrodes 18 and 22. Sensor 26 is composed of a material which exhibits a change in conductivity in response to exposure of the material to a gas to be sensed.

Overlying sensor 26, on the side thereof opposite surface 16, is a molecular sieve 28. Sieve 28 is composed of a porous solid material that has a pore size no larger than the molecular size of the gas which is to be sensed. In the direction of the spacing between electrodes 18 and 20, sieve 28 extends on outwardly beyond the edges of sensor 26 so as to cover entirely the material of the sensor. In FIG. 1 as drawn, the ends of sensor 26 are, for clarity of explanation, shown as being exposed; in practice, this is not to be the case. For reasons which will become apparent, either sieve 28 extends down over those ends of sensor 26 so as entirely to cover the same or some other material is formed over those ends of sensor 26 in order to passivate them and, thus, seal the ends as against direct exposure to the gas to be detected. In any case, sensor 26 is not exposed to such gas except through the pores which exist in the material of sieve 28.

In general with use of sieve 28, sensor 26 preferably is selected from among the semiconducting metal oxides. Those oxides are polycrystalline thin films in which the surface of each crystallite, both the gas-solid interface and the intergranular facets, constitute the active area. The primary physical mechanism of sensitivity to the gas is a charge transfer between individual crystallites and the adsorbed gas species by way of an electrochemical interaction, a displacement interaction, or both as between the gas constituents and ionized adsorbed oxygen. In sufficiently thin films or in polycrystalline films of critical grain radius to doping-level ratio, the surface interactions can dominate the bulk electrical characteristics of the sensor. The charge transfer effects conductivity in a thin film, which may be measured as a change in resistance. One example of this mechanism is the response of sensor 26 to carbon monoxide as illustrated by the following reaction:

$$CO_{gas} + O_{ads}^- = CO_2 + e^- \tag{1}$$

Equation (1) generalizes the oxidation reaction of gaseous carbon monoxide at the sensor surface with the ionized adsorbed oxygen forming carbon dioxide and donating an electron to the bulk semiconductor film. The product, carbon dioxide, is adsorbed on the sensor surface. Subsequent desorption of the carbon dioxide is defined by an isotherm which relates the ratio of the quantity of the adsorbed gas species to its partial pressure in the gas phase. The resistance of sensor 26 remains low as long as the surface is depleted of ionized oxygen.

A secondary mechanism involved is the polar nature of adsorbed gas species which sets up a localized field at the surface, resulting in an accumulation or depletion of charges at the surface. In such polycrystalline metal-oxide-based thin films, the sensitivity is highly dependent upon the average grain size, size distribution and doping level. For such films as used in this context, the most efficient grain structure is that in which the grains are distinct, equisized and spherical with all grains being interconnected and containing a specific doping level.

In the present embodiment, sensor 26 is composed of a thin film of zinc oxide doped with gallium oxide. The gallium oxide stabilizes the grain structure of the zinc oxide film and increases the sensitivity of that film to the adsorbed gas species. In the present technique, the zinc oxide material of sensor 26 is deposited upon surface 16 by the well-known technique of radio-frequency sputtering. Suitable apparatus and mode of operation for use of this sputtering technique is described in Leary, D. J., "Metals and Semiconducting Metal Oxides in Conjunction With Silicon for Solid State Gas Detection," Ph.D. thesis, Carnegie-Mellon Univ., Pittsburgh, Pa., published Aug. 22, 1979 and available through University Microfilms International. As merely one additional example of a known radio-frequency sputtering technique, inclusion by cross-reference is made to U.S. Pat. No. 3,669,860 issued June 13, 1972, in the name of Knowles et al, and to the references cited therein.

Using that approach, the temperature of substrate 12 during the sputtering operation is elevated to about 350° Centigrade. The gallium oxide dopant may be incorporated into the film which forms sensor 26 either by including the gallium oxide material into the sputtering target or by including a separate gallium oxide target in the sputtering apparatus all in accordance with well known techniques, as such.

The final concentration of the gallium oxide dopant as an impurity in the zinc oxide basic material of sensor 26 preferably is about 1.5 atomic percent. The grain size preferably is about fifty nanometers (nm) in thickness. In general, the dopant impurity may be introduced so as to be within a range of approximately ±1 percent, and the grain size may be within a range of approximately ±10 percent.

It is to be noted that the use of sputtering to deposit sensor 26 on surface 16 enables precise control of the level of the doping with the gallium oxide impurity. It also should be noted that gallium appears to be unique in its property of influencing the grain structure of the zinc oxide. Thus, the described technique achieves complete control of both crystal structure and doping level. Moreover, the technique described herein permits operation of the zinc oxide material of sensor 26 at elevated temperatures. This contrasts with earlier-known zinc oxide thin films which experienced short term deterioration and recrystallization when operated above two hundred degrees Centigrade. When prepared as described herein, the resulting sensor exhibits an optimum of suitability for use in detecting gases.

The formation of oxide layer 14 and of electrodes 18 and 20 is not critical and may be accomplished in accordance with any known technique for depositing such elements. For example, electrodes 18 and 20 may be patterned and vacuum evaporated by any standard technique. Leads 22 and 24 may be bonded to electrodes 18 and 20 by well-known wire bonding techniques. Electrodes 18 and 20 conveniently may be of platinum or any other compatible metal.

In itself, molecular sieve 28 may take a variety of different forms. As such, it is well known that the properties necessary to achieve molecular sieve action exist in many different materials. The term "molecular sieve" defines a porous solid material which exhibits the property of acting as a sieve on a molecular scale. The physical properties of a wide variety of molecular sieve materials are well documented. For use in gas monitoring apparatus, however, it is preferred that the molecular sieve material be capable of being processed in accordance with integrated circuit technology and particularly in accordance with the formation of thin films as consistent with silicon planar techniques. Of course, it is necessary in accordance with the present embodiment that the resulting molecular sieve exhibit characteristics appropriate to the separation of the constituents of different gases.

Examples of suitable molecular sieve materials produced and in accordance with the present embodiment, together with their screening or separation properties and examples of gases which will pass through the resulting sieve 28, all as associated with the use of zinc oxide as the basic sensor material, are set forth in the following table.

TABLE 1

| Molecular Sieve Material | Effective Pore Diameter (nm) | Examples of Gases Which Pass Through The Sieve |
| --- | --- | --- |
| Pd, Pt | 0.11 | Dissociated Hydrogen |
| Zeolite 3A | 0.30 | $H_2$, $O_2$, CO, $NH_3$ |
| Zeolite 4A | 0.40 | Above gases and $H_2S$, $CH_4$, $SO_2$, $CO_2$, some ethanes, e.g.: $C_2H_4$ $C_2H_6$, $C_3H_6$. |
| Zeolite 5A | 0.50 | Above gases and some of the smaller paraffins |
| Zeolite 10X | 0.80 | Isoparaffins and Oleffins $C_6H_6$ |
| Zeolite 13X, BeO | 1.0 | Larger hydrocarbons and halogenated hydrocarbons |

Table 1 was determined with sensor 26 operating at approximately 200° Centigrade. In all cases, the molecular sieve material is a passivation layer with respect to sensor 26, except, of course, to the extent that desired gases are admitted through the pores in molecular sieve 28.

Molecular sieve 28 acts to screen out gas species that have a larger molecular size than the molecular-sieve pore size. The gas species which pass are adsorbed on the active surface of sensor 26. In operation of sensor 26, it basically is only necessary to measure the resistance which appears between electrodes 18 and 20. Of course, that at least usually means applying a potential across those electrodes and actually reading the current which flows as a result. The adsorption of even a very low concentration of gas constituents produces significant changes in the resistance of sensor 26.

Gases which chemically react with ionized adsorbed oxygen effect a change in sensor resistance. Those gases which displace the ionized adsorbed oxygen and in themselves are adsorbed as charged species, so as to result in a net depletion of electrons from sensor 26, act to cause the latter to exhibit an increased resistance. Conversely, those gases which displace the ionized adsorbed oxygen and are themselves adsorbed as charged species, so as to result in a net contribution of electrons, act to decrease sensor resistance.

There is in operation a temperature dependence; it is basically the temperature dependence characteristic of the ionized absorbed oxygen which dictates the overall response characteristic. Illustrative response characteristics for the device in FIG. 1, when operated at a temperature of 200° Centigrade, are shown in FIG. 2. Initially, device 10 is equilibrated in dry air prior to exposure to the gas under test which begins at time $t_o$. In FIG. 2, time in seconds is represented along the abscissa, and resistance in kilo-ohms is depicted along the ordinate. In the case of each of the three curves 20, 32 and 34, the response is represented in terms of a change in measured resistance produced by exposing sensor 26 through sieve 28 beginning at the time $t_o$ to a dry air sample containing the particular gas represented. Following the exposure of device 10 to the gas, the test chamber is purged by the introduction of ambient air so as to restore the original ambient conditions. The time at which the purging begins is indicated by the respective points 36, 38 and 40.

Curve 30 represents exposure of device 10 to twenty parts-per-million of carbon monoxide in dry air. As indicated, there is an immediate decrease in resistance. The interaction of the carbon monoxide with the ionized adsorbed oxygen releases electrons into the bulk. Upon subsequent purging, as represented at 36, the resistance of sensor 26 returns essentially to its original value.

Curve 32 represents exposure of device 10 to one hundred parts-per-million of hydrogen in dry air. Again, there is an immediate decrease in sensor resistance. It will be observed that both the adsorption and desorption time constants for hydrogen are faster than in the case of carbon monoxide as illustrated by curve 30.

As represented by curve 34, an opposite response occurs when the relative concentration of oxygen in the ambient air is increased by just one percent. That is, the resistance of sensor 26 increases as represented by curve 34. It may be noted that the rates of both adsorption and desorption for this example are longer than for either of those rates in the case of hydrogen or carbon monoxide. The adsorption isotherm for oxygen dictates an increase in the equilibrium surface coverage of ionized adsorbed oxygen, resulting in a decrease of electrons from the bulk and a consequent increase in measured resistance.

In order, particularly, to be consistent with the use of fabrication techniques at least analogous to those presently employed in thin-film planar silicon technology, the deposition of certain of the materials of which sieve 28 may be formed appears to require careful attention in order to achieve consistent results. This specifically applied to use of the zeolites. To that end, these materials are first mixed with a binder. Surface 16 and a portion of electrodes 18 and 20 are then masked in accordance with a normal approach, or patterning otherwise is achieved, and the mixture is sprayed into place in order to form sieve 28. While this approach is rather unique in the deposition of materials on semiconductor substrates, it readily accomplishes the desired result and also avoids interference with previously-deposited elements as otherwise may occur with the adoption of more usual material-application techniques.

In more detail, molecular sieve 28 preferably is deposited by a planar technique known as spray pyrolysis. Apparatus and mode of operation are described for example, in Aranovich, J., Ortiz, A., Bube, R., "Optical and Electrical Properties of Zno Films Prepared by Spray Pyrolysis for Solar Cell Applications," J. Vac, Sci, Technol., 16 (4), July (1979), pp. 994–1003 and Maudes, J., Rodriquez, T., "Sprayed SnO Films; Growth Mechanism and Film Structure Characterization," Thin Solid Films, 69 (1980) pp. 183–189.

This approach involves forming an aqueous solution of the sieve material in a binder. A gas stream serves as a carrier through a spray nozzle. During the spray operation, device 10 is maintained at a temperature above 200° Centigrade, and preferably at about 250° Centigrade. This approach relies upon pyrolytic decomposition of the binding agent which is dissolved in high purity de-ionized water along with the molecular sieve material.

Any of a number of well-known soluable salts may be used as the binding agent. The nitrate family is representative. Aluminum nitrate, for example, is mixed with the molecular sieve material in a two-to-one ratio by weight. The powder mixture (0.8 gm) is then dissolved in sufficient water (100 $CM^3$) and stirred at 50° Centigrade for about thirty minutes. Nitrogen gas serves well as the carrier. The aforementioned ratio of binder to sieve material appears to apply also in the case of use of other salts as binders.

Of course, the thickness of the different layers and the overall size of device 10 may be varied as desired for a particular ultimate utility. In the specific device of FIG. 1 as employed to produce the results of FIG. 2, the approximate thicknesses of layer 14, sensor 26, molecular sieve 28, and electrodes 18 and 20 respectively were 0.5 micron, 0.5 micron, 0.1 micron and 0.1 micron. The length and width of device 10 each were about one millimeter.

Thus far, attention has been directed primarily to device 10 as a discrete sensing element. Whether used in that form or created into an array on a single chip, the approach herein presented lends itself well to system application. As shown in FIG. 3, a plurality of gas sensing devices 10a-10i are distributed in an array. Devices 10a-10i are connected through cables 44 to an integrated signal processing and combinational logic network 46. For purpose of initial discussion, it may be assumed that each of devices 10a-10i is fabricated in the manner of device 10 of FIG. 1, except that individually different ones of devices 10a-10i have a molecular sieve 28 with respectively different pore sizes. For example, device 10a might be selected to have the largest pore size so as to pass all gases exhibiting molecular sizes no larger than the pores in the sieve of that device. The remaining ones of devices 10b-10i then might successively have smaller and smaller pore sizes so as to screen out more and more of the gases possibly present with the last device in the series having the smallest pores and, therefore, passing only those gases with the very smallest molecular sizes. Of course, the use of a total of nine devices in FIG. 3 is purely arbitrary and illustrative. For any given task, the total number of devices might be smaller or larger.

As a first alternative, it is to be noted that not all of devices 10a-10i need be fabricated in the manner of device 10 of FIG. 1. For example, a different kind of gas detecting and/or discriminating device might, in a given application, be more suitable for some particular gas, whether it is solid state, catalytic or of other type. In any case, it is to be noted that cables 44 are depicted in single-line representation. For device 10 in FIG. 1, of course, two leads are necessary to permit the desired resistance determination. Thus, each one of cables 44 may carry a pair of respective leads. Alternatively, one lead from each of the different ones of devices 10a-10i may be connected in common to network 46 with one similar lead from each of the others of the devices.

Whatever the specific nature and the actual number of devices 10a-10i, each different one of those devices is uniquely and fully characterized by a particular gas-response function. At least with the approach of device 10 in FIG. 1, each such device, operated at a given temperature, is further characterized with constant sensitivity, stability and reliability with respect to the limits on molecular sizes of the gases it will sense. Those characteristics permit unambiguous decoding by network 46.

Having, therefore, a plurality of different possible inputs each of which exhibits a unique response characteristic, it is but an exercise of routine programming of a microcomputer included within network 46 so as to correlate the known individual different response functions of devices 10a-10i with the actual responses being received by network 46 at any time. Thus, qualitative determination is enabled by use of conventional signal processing. Just as conventionally, straight-forward determination of level of any given response permits quantitative determination, so as to yield a measurement of the concentration of any particular gas species detected by a given one of devices 10a-10i.

In connection with the qualitative determination effected by network 46, it is to be noted that the electrical analog of the array of devices shown in FIG. 3, each of a kind fabricated in accordance with device 10 of FIG. 1, is that of a low-pass filter. The individual different ones of devices 10a-10i effectively have respectively different cut-off frequencies. With an analog-type signal, of course, quantitative determination requires only effectively direct measurement of signal level. The existence of effectively different cut-off frequencies permits readily-separable qualitative discrimination of the myriad of different components of the analog signal received from the device array of FIG. 3. It will be observed that, using device 10 of FIG. 1, the just-discussed low-pass filters are, in fact, molecular sieve materials 28; similarly, the analog signal is the gas ambient comprised of different gas constituents (frequencies).

A particular feature of the devices of FIG. 1, as intended for use in an array of devices as illustrated in FIG. 3, is that all of the devices may be fabricated on a single substrate or chip. Moreover, if desired, a portion or all of the processing and logic circuitry of network 46 may be fabricated on that very same chip so as to reduce both size and cost of the instrumentation.

As already indicated, device 10 is sensitive to changes in temperature. That is, its response characteristic will exhibit a change with a change in temperature of the device. For one or more discrete versions of device 10, of course, a conventional temperature-controlled oven may be employed. The oven temperature is sensed and that measurement is employed to control operation of a heater which maintains constant the temperature within the oven at whatever value is desired for the particular device 10 enclosed and heated. Preferably for that case, however, a thin-film element would be deposited directly on surface 16 or otherwise located so as to deliver heat to substrate 12 and thus to the entire assembly. The use of such thin film heating elements in integrated-circuit technology is now well known, including the provision of sensing of the temperature and control for maintaining a constant temperature of the device. In a simplification, the instantaneous resistance of the heater film is in itself used as a determinate of temperature.

However, when an array, such as illustrated in FIG. 3, is disposed on a common substrate, it is preferred to employ individual thin-film heating elements for each different one of devices 10a-10i. That allows the additional flexibility of individually selecting the temperature at which each different one of devices 10a-10is operated, as well as allowing for compensation of the operation of any individual one of those devices for the possible cooling or heating effects induced by gas species actually sensed by any particular device within the array. With the provision of individual different heating elements for respective ones of the devices in the array, it is further preferred to include thermal isolation between the adjacent different ones of the devices. As is well known generally in integrated circuit technology, this may be accomplished, for example, by etching a well surrounding each individual device and subsequently depositing a low-thermal-conductivity medium in that well.

As embodied, substrate 12 is composed of silicon. However, other suitable substrate materials may be utilized. Silicon is presently preferred because it lends itself to the fabrication of device 10 by the adoption of planarprocessing techniques now well understood and for which processing machinery already is readily available in the semiconductor industry. Those fully-developed techniques are used in accordance with the processing of the present embodiment for the disposition of all components, even including molecular sieve 28. Moreover, the present preference for those techniques additionally stems from the capability of being able also to employ the same well-known technology for the fabrication of the integrated circuitry which forms all or part of network 46.

It will thus been seen that sieve 28 is a material advantageously useful for the screening and separation of gas constituents based on gas molecule size so as to effect sensor selectivity. This distinguishes from prior-known techniques which rely upon achieving selectivity by dependence upon preferential gas molecular adsorption on a sensor surface. In the approach of the present embodiment, the gas constituents are separated before they reach the sensor surface. Moreover, this approach of screening and separation prior to sensing is applicable regardless of the specific nature of sensor 26.

Although the particularly embodied form of sensor 26 is preferred by reason of the unique capability of the gallium oxide dopant to enable controlled influence upon the grain structure of the zinc oxide sensing film, it is comtemplated that other sensors, such as different and known metal oxides, may be substituted in a given application. Conversely, the herein disclosed form of sensor 26, specifically composed of a zinc oxide film doped with gallium oxide, is contemplated for use in other monitoring apparatus that may rely upon a different manner of discrimination as between various gas constituents or for use in a situation where discrimination is not necessary because only an already-identified gas species is to be monitored.

It is to be observed that devices fabricated in accordance with the present embodiment exhibit a high degree of selectivity, long-term stability and reproducibility. While a single gas species may be identified and measured, the system approach as exemplified in FIG. 3 actually does not require absolute selectivity. By selectively separating detected gas species in accordance with molecular sizes and correlating the signals from an array as discussed in connection with FIG. 3, both qualitative and quantitative determination is achieved without the need for such absolute selectivity.

Of course, the availability of now-conventional integrated circuit technology for the fabrication of the devices enables the achievement of cost-effective portable instrumentation. As indicated, response function of device 10 is well characterized with respect to all of stability, sensitivity and reproducibility. As a result, the desired detection and discrimination of even trace levels of gas impurities requires only the association of now standard signal processing techniques. Thus, standardized integrated circuits and fabrication by means of conventional integrated-circuit processing may be realized by an approach which is both low in cost and achieves the objective of compactness and simplicity of signal processing as required for portability of the ultimate instrumentation.

While a particular embodiment of the invention has been shown and described, and numerous modifications and alternatives have been described and further ramifications have been mentioned, it will be obvious to those skilled in the art that changes and modifications may be made without departing from the invention in its broader aspects. Therefore, the aim in the appended claims is to cover all such changes and modifications as fall within the true spirit and scope of that which is patentable.

I claim:

1. Gas monitoring apparatus comprising:
   a support which includes an electrically insulating surface;
   a pair of electrodes spaced apart on said surface;
   a sensor disposed on said surface in a position bridging said electrodes, said sensor being composed of a material which exhibits a change in electrical conductivity in response to exposure of said material to a gas to be sensed;
   and a molecular sieve integrally overlying said sensor on the side thereof opposite said surface, said sieve being composed of a porous solid material and having a discrete pore size no larger than the molecular size of said gas to be screened.

2. Apparatus as defined in claim 1 in which said molecular sieve consists essentially of palladium, platinum, zeolite or beryllium oxide.

3. Apparatus as defined in claim 1 in which said sensor consists essentially of zinc oxide doped with gallium oxide as an impurity.

4. Apparatus as defined in claim 1 in which the material of said molecular sieve is deposited by spray pyrolysis over said sensor.

5. Apparatus as defined in claim 4 in which the source material for spray pyrolysis deposition is the material of said sieve mixed with a binder consisting essentially of a soluable salt.

6. Apparatus as defined in claim 1 in which the material of said sieve passivates said sensor except for gases having a molecular size smaller than said pore size.

7. Apparatus as defined in claim 1 in which said support includes a substrate of silicon and said surface is an oxide layer formed on said silicon.

8. Gas monitoring apparatus comprising:
an array of a plurality of devices each including:
a support which includes an electrically insulating surface;
a pair of electrodes spaced apart on said surface;
a sensor disposed on said surface in a position bridging said electrodes, said sensor being composed of a material which exhibits a change in electrical conductivity in response to exposure of said material to a gas to be sensed;
a molecular sieve integrally overlying said sensor on the side thereof opposite said surface, said sieve being composed of a porous solid material and having a discrete pore size no larger than the molecular size of said gas to be screened;
said sensors in all of said devices being identically composed of inorganic material and said molecular sieves in said plurality of devices individually having different discrete pore sizes respectively no larger than the molecular sizes of corresponding different gas constituents to be screened;
and means coupled to the different ones of said electrodes for responding to changes in electrical parameters respectively presented between said different pairs of electrodes to enable determination and analysis of different gas constituents correspondingly passed to different ones of said sensors by respective different ones of said sieves.

* * * * *